US008470874B2

(12) United States Patent
Musty et al.

(10) Patent No.: US 8,470,874 B2
(45) Date of Patent: Jun. 25, 2013

(54) PHARMACEUTICAL COMPOSITIONS COMPRISING CANNABICHROMENE TYPE COMPOUNDS (75) Inventors: Richard E. Musty, Burlington, VT (US); Richard Deyo, Winona, MN (US)

(73) Assignee: GW Pharma Limited, Salisbury (GB)

( * ) Notice: Subject to any disclaimer, the term of this patent is extended or adjusted under 35 U.S.C. 154(b) by 141 days.

(21) Appl. No.: 10/561,756

(22) PCT Filed: Jun. 24, 2004

(86) PCT No.: PCT/GB2004/002714
§ 371 (c)(1),
(2), (4) Date: Dec. 21, 2005

(87) PCT Pub. No.: WO2005/000830
PCT Pub. Date: Jan. 6, 2005

(65) Prior Publication Data
US 2006/0153941 A1    Jul. 13, 2006

Related U.S. Application Data (60) Provisional application No. 60/482,110, filed on Jun. 24, 2003.

(51) Int. Cl.
*A61K 31/35* (2006.01)

(52) U.S. Cl.
USPC ............................................. 514/451; 514/456

(58) Field of Classification Search
USPC ................................................. 514/456, 451
See application file for complete search history.

(56) References Cited

U.S. PATENT DOCUMENTS

| | | | |
|---|---|---|---|
| 4,837,228 A | 6/1989 | Elsohly et al. | |
| 6,328,992 B1 * | 12/2001 | Brooke et al. | 424/449 |
| 6,541,510 B2 | 4/2003 | Travis | |
| 2002/0068738 A1 * | 6/2002 | Travis | 514/232.8 |
| 2003/0232101 A1 | 12/2003 | Travis | |
| 2005/0042172 A1 | 2/2005 | Whittle | |
| 2006/0257463 A1 | 11/2006 | Elsohly et al. | |
| 2008/0031977 A1 | 2/2008 | Musty et al. | |
| 2011/0098348 A1 | 4/2011 | De Meijer | |

FOREIGN PATENT DOCUMENTS

| | | |
|---|---|---|
| CA | 2 322 549 A1 | 3/2002 |
| WO | WO 02/26728 A2 | 4/2002 |
| WO | WO 02/64109 A3 | 8/2002 |
| WO | WO 2004/016254 A1 | 2/2004 |
| WO | WO 2009/125198 A2 | 10/2009 |

OTHER PUBLICATIONS

Turner et al. Biological activity of cannabichromene, its homologs and isomers. J Clin Pharmacol. 1981; 21:283S-291S.*
Harvey et al. "Identification of cannbichromene metabolites by mass specrometry: identification of eight new dihydroxy metabolites in the rabbit". Biological Mass Spectromety, vol. 20, 275-285 (1991).*
Chen et al. Marijuana use and risk of major depressive episode. Soc. Psychiatry Psychiatr Epidemiol (2002) 37: 199-206.*
Rowan, M.G. et al., "Cannabinoid patterns in seedlings of *Cannabis sativa* L. and their use in the determination of chemical race," *J. Pharma. Pharmac.* 1977; 29: 491-494.
Vogelmann, A.F., "Cannabinoid composition in seedlings compared to adult plants of *Cannabis sativa*," *Journal of Natural Products* Nov.-Dec. 1988; 51(6): 1075-7079.
The United Kingdom Parliament, Select Committee on Science and Technology Ninth Report (1998) at http://www .parliament.the-stationery-office.co.uk/pa/Id199798/Idselect/Idsetech/151/15101.htm.
The United Kingdom Parliament, Select Committee on Science and Technology Second Report (14 Mar. 2001) at http://www.publications.parliament.uk/pa/Id200001/Idselect/Idsctech/50/5001.htm.

(Continued)

*Primary Examiner* — Renee Claytor
(74) *Attorney, Agent, or Firm* — Wolf, Greenfield & Sacks, P.C.

(57) ABSTRACT

The invention relates to the use of cannabichromene type compounds and derivatives thereof in the treatment of mood disorders.

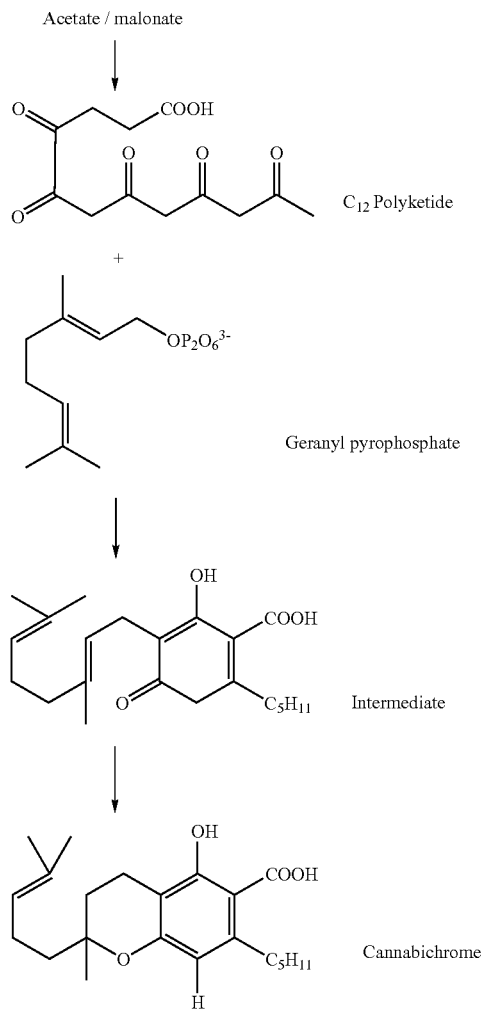

8 Claims, 8 Drawing Sheets

OTHER PUBLICATIONS

Mechoulam, R. "Plant cannabinoids: a neglected pharmacological treasure trove," *British Journal of Pharmacology* 2005; 146:913-915.

Henry, John, *Cannabis damages mental health*, BBC News, Apr. 2003 [http://news.bbc.co.uk/2/hi/health/2923647.stm].

Rey et al., *Mental health of teenagers who use cannabis*, Br J Psychiatry. Mar. 2002; 180:216-21.

Burstein et al., Prostaglandins and *Cannabis* .II. Inhibition of biosynthesis by the naturally occurring cannabinoids. Biochem Pharmacol. Nov. 15, 1973;22(22):2905-10.

De Meijer et al., the inheritance of chemical phenotype in *Cannabis sativa* L. (III): variation in cannabichromene proportion. Euphytica. Aug. 23, 2008;165(2):293-311.

Gaoni et al., The isolation and structure of delta-l-tetrahydrocannabinol and other neutral cannabinoids from hashish. J Am Chem Soc. Jan. 13, 1971;93(1):217-24.

Gruber et al., Do patients use marijuana as an antidepressant? Depression. 1996;4(2):77-80. Review.

Hatoum et al., Cannabichromene and delta 9-tetrahydrocannabinol: interactions relative to lethality, hypothermia and hexobarbital hypnosis. Gen Pharmacol. 1981;12(5):357-62.

Steru et al., The tail suspension test: a new method for screening antidepressants in mice. Psychopharmacology (Berl). 1985;85(3):367-70.

Turner et al., Constituents of *Cannabis sativa*. L. XVII. A review of the natural constituents. J Natural Prod. May 28, 1980;43(2):169-234.

Turner et al., Constituents of *Cannabis sativa* L.X. Cannabinoid profile of a Mexican variant and its possible correlation to pharmacological activity. Acta Pharm Jugoslav. 1975;25:7-16.

Turner, Cannabinoid synthesis in *Cannabis sativa* L. Physiological section. Jun. 1985:911. Abstract #325.

Walsh et al., Mechanisms mediating the production of environmentally induced brain changes. Psychol Bull. Nov. 1975;82(6):986-1000.

Wirth et al., Anti-inflammatory properties of cannabichromene. Life Sci. Jun. 9, 1980;26(23):19915.

Zimmerman, Is marijuana the right medicine for you? Keats Publishing, Inc. New Canaan, CT. 1998:166-7.

* cited by examiner

FIG. 1

| Test Article | Count | Mean | Std. Dev. | Std. Error |
|---|---|---|---|---|
| CBC 0mg (Control) | 8 | 462.500 | 234.557 | 82.928 |
| CBC 5mg | 8 | 644.625 | 280.245 | 99.117 |
| CBC 10mg | 8 | 770.750 | 380.570 | 134.552 |
| CBC 20mg | 8 | 606.750 | 269.183 | 95.170 |
| CBC 40mg | 8 | 916.125 | 536.324 | 189.619 |
| CBC 80mg | 8 | 670.625 | 608.221 | 215.039 |
| Imipramine 30mg | 8 | 733.500 | 205.358 | 72.605 |

|  | Mean Difference | Critical Difference | P-Value |
|---|---|---|---|
| CBC 0mg; CBC 5mg | -182.125 | 389.273 | 0.3517 |
| CBC 0mg; CBC 10mg | -308.250 | 389.273 | 0.1180 |
| CBC 0mg; CBC 20mg | -144.250 | 389.273 | 0.4600 |
| CBC 0mg; CBC 40mg | -453.625 | 389.273 | 0.0233* |
| CBC 0mg; CBC 80mg | -208.125 | 389.273 | 0.2879 |
| CBC 0mg; Imipramine 30mg | -271.000 | 389.273 | 0.1681 |
| CBC 5mg; CBC 10mg | -126.125 | 389.273 | 0.5180 |
| CBC 5mg; CBC 20mg | 37.875 | 389.273 | 0.8458 |
| CBC 5mg; CBC 40mg | -271.500 | 389.273 | 0.1673 |
| CBC 5mg; CBC 80mg | -26.000 | 389.273 | 0.8938 |
| CBC 5mg; Imipramine 30mg | -88.875 | 389.273 | 0.6484 |
| CBC 10mg; CBC 20mg | 164.000 | 389.273 | 0.4013 |
| CBC 10mg; CBC 40mg | -145.375 | 389.273 | 0.4566 |
| CBC 10mg; CBC 80mg | 100.125 | 389.273 | 0.6076 |
| CBC 10mg; Imipramine 30mg | 37.250 | 389.273 | 0.8483 |
| CBC 20mg; CBC 40mg | -309.375 | 389.273 | 0.1167 |
| CBC 20mg; CBC 80mg | -63.875 | 389.273 | 0.7430 |
| CBC 20mg; Imipramine 30mg | -126.750 | 389.273 | 0.5160 |
| CBC 40mg; CBC 80mg | 245.500 | 389.273 | 0.2110 |
| CBC 40mg; Imipramine 30mg | 182.625 | 389.273 | 0.3504 |
| CBC 80mg; Imipramine 30mg | -62.875 | 389.273 | 0.7469 |

\* Statistically significant

FIG. 4

| Test Article | Count | Mean | Std. Dev. | Std. Error |
|---|---|---|---|---|
| CBC 0mg (Control) | 8 | 13.334 | 5.755 | 2.035 |
| CBC 5mg | 8 | 18.364 | 9.193 | 3.250 |
| CBC 10mg | 8 | 23.962 | 11.374 | 4.021 |
| CBC 20mg | 8 | 31.350 | 6.951 | 2.458 |
| CBC 40mg | 8 | 23.853 | 12.195 | 4.312 |
| CBC 80mg | 8 | 30.250 | 16.628 | 5.879 |
| Imipramine 30mg | 8 | 23.874 | 12.557 | 4.440 |

| | Mean Difference | Critical Difference | P-Value |
|---|---|---|---|
| CBC 0mg; CBC 5mg | -5.030 | 11.255 | 0.3735 |
| CBC 0mg; CBC 10mg | -10.628 | 11.255 | 0.0636 |
| CBC 0mg; CBC 20mg | -18.016 | 11.255 | 0.0023* |
| CBC 0mg; CBC 40mg | -10.519 | 11.255 | 0.0663 |
| CBC 0mg; CBC 80mg | -16.917 | 11.255 | 0.0040* |
| CBC 0mg; Imipramine 30mg | -10.540 | 11.255 | 0.0658 |
| CBC 5mg; CBC 10mg | -5.598 | 11.255 | 0.3224 |
| CBC 5mg; CBC 20mg | -12.987 | 11.255 | 0.0246* |
| CBC 5mg; CBC 40mg | -5.489 | 11.255 | 0.3318 |
| CBC 5mg; CBC 80mg | -11.887 | 11.255 | 0.0389* |
| CBC 5mg; Imipramine 30mg | -5.510 | 11.255 | 0.3300 |
| CBC 10mg; CBC 20mg | -7.389 | 11.255 | 0.1932 |
| CBC 10mg; CBC 40mg | 0.109 | 11.255 | 0.9846 |
| CBC 10mg; CBC 80mg | -6.289 | 11.255 | 0.2670 |
| CBC 10mg; Imipramine 30mg | 0.088 | 11.255 | 0.9875 |
| CBC 20mg; CBC 40mg | 7.497 | 11.255 | 0.1868 |
| CBC 20mg; CBC 80mg | 1.100 | 11.255 | 0.8451 |
| CBC 20mg; Imipramine 30mg | 7.476 | 11.255 | 0.1881 |
| CBC 40mg; CBC 80mg | -6.397 | 11.255 | 0.2589 |
| CBC 40mg; Imipramine 30mg | -0.021 | 11.255 | 0.9970 |
| CBC 80mg; Imipramine 30mg | 6.377 | 11.255 | 0.2604 |

* Statistically significant

FIG. 7

CHROMATOGRAPHIC CONDITIONS:

Stationary phase: SIL G/UV $_{254}$
  Mobile phase: Hexane: diethyl ether 80:20
  Development distance: double development.
  Visualisation: 0.1% w/v Fast Blue B salt in water Standards   1 mg/ml CBD (BN 10601/C) in MeOH
  5 ul applied to TLC plate.
   1 mg/ml d9 THC (BN 10601/B) in MeOH
  5 ul applied to TLC plate.

Samples   1 mg/ml CBC STARTING MATERIAL in MeOH
  5 ul applied to TLC plate.
   1 mg/ml ENRICHED CBC EXTRACT in MeOH
  5 ul applied to TLC plate.

PHARMACEUTICAL COMPOSITIONS COMPRISING CANNABICHROMENE TYPE COMPOUNDS

RELATED APPLICATIONS

This application is a national stage filing under 35 U.S.C. §371 of international application PCT/GB2004/002714, filed June 24, 2004, which was published under PCT Article 21(2) in English.

FIELD OF THE INVENTION

The present invention relates to the use of cannabichromene type compounds and derivatives thereof in the treatment of mood disorders.

BACKGROUND TO THE INVENTION

Mood disorders are generally classified by type and include, but are not limited to:

A morbid or clinical depression, which is usually diagnosed when sadness or elation is overly intense and continues beyond the expected impact of a stressful event. Symptoms often recur on an episodic basis or pursue a low-grade intermittent chronicity, which impairs the functioning of the sufferer.

Bipolar mood disorder, which commonly begins with depression and is characterised by periods of elation during the course of the illness.

Unipolar mood disorder, which is characterised as syndromal depression of episodes that last for typically 6 to 9 months.

The pharmaceuticals used in the treatment of Unipolar and Bipolar Mood Disorders can be grouped into three classes; the heterocylic antidepressants (HCAs), monoamine oxidase inhibitors (MAOIs) and lithium salts.

HCAs are the largest class of antidepressants and include tricyclic antidepressants such as imipramine. The HCAs have no immediate effect on euphoria and therefore have a low abuse potential. This group of antidepressants work by increasing the availability of the biogenic amines norepinephrine and/or serotonin (5-HT) by blocking re-uptake in the synaptic cleft. The side effects of HCAs include tachycardia, postural hypotension and cardio-toxicity. HCAs are also commonly associated with blurred vision, xerostomia, constipation, urinary hesitation, sedation and weight gain. The hypotensive side effects of HCAs often make them unsuitable for patients with mental disorders and the elderly.

MAOIs such as phenelzine are often prescribed for panic disorder. They work by inhibition of the oxidative deamination of the 3 classes of biogenic amines; noradrenergic, dopaminergic and 5-HT. MAOIs are underused because of clinicians' fears of paradoxical hypotension that may result from dietary or drug interactions, popularly known as the "cheese reaction" due to the high tyramine content in mature cheese. Other common side effects are postural hypotension erectile difficulties, anxiety, nausea, dizziness, insomnia, edema, weight gain and less commonly hepatotoxicity.

Lithium is used to stabilise the often unpredictable mood swings in bipolar mood disorder. The precise mechanism for its actions are unknown, but could be due to hyperpolarisation of the neuronal membrane. The most common acute benign side effects of lithium are tremor, fasciculation, nausea, diarrhoea, polyuria, polydipsia and weight gain. Lithium toxicity is more likely in elderly patients.

SUMMARY OF THE INVENTION

Surprisingly, it has been found that cannabichromene (CBC) and cannabichromene type compounds (including cannabichromene propyl analogue (CBC-V)) and derivatives thereof, appear to be a new class of compounds that may be useful in the treatment of mood disorders, particularly depression

The cannabichromene type compounds have the general formula 1.

Formula 1 where;
$R^1$ is OH;
$R^2$ is H or COOH;
$R^3$ is a C1 to C8 alkyl group; and
and $R^4$ is H According to a first aspect of the present invention there is provided a pharmaceutical composition (excluding smoked *cannabis*) comprising at least one cannabichromene and cannabichromene type compound of the general formula 1

Formula 1 where;
$R^1$ is OH;
$R^2$ is H or COOH;
$R^3$ is a $C_1$-$C_8$ alkyl group; and
and $R^4$ is H
or pharmaceutically acceptable derivative thereof for use in treating mood disorders.
Where $R^2$ is COOH, then pharmaceutically acceptable salts may also be utilised in the composition. The term "pharmaceutically acceptable salts" refers to salts prepared from pharmaceutically acceptable non-toxic bases or acids, including inorganic bases or acids and organic bases or acids, as would be well known to persons skilled in the art.
$R^3$ is preferably a C1-C5 alkyl group, more preferably C3-C5 alkyl group, and the alkyl group is preferably straight chain, with n-pentyl and n-propyl groups being the most preferred.
$R^2$ may be H or COOH. As discussed below, the pharmacologically active forms of the cannabichromenes are the neutral cannabinoids, but the invention also encompasses formulations including the corresponding cannabinoid acids. The decision whether to use the acid or neutral cannabinoid form may depend upon the nature of the formulation and it's intended route of administration. For example, compositions that are intended to be administered in the form of an inhaled vapour may contain the cannabinoid acid form, since the composition will be heated during vaporisation, thus facilitating the decarboxylation of free cannabinoid acids to the corresponding neutral cannabinoid form.

The "cannabichromene or cannabichromene type compounds" of formula 1 included in the compositions of the invention may be naturally occurring compounds or synthetic compounds. "Naturally occurring" cannabichromenes include cannabichromenes obtainable from *cannabis* plant material.

Natural cannabichromenes include cannabichromene (CBC) (Formula 2) and cannabichromene propyl analogue (CBC-V) (Formula 3)

Formula 2 where $R^1$ is either H or COOH
$C_5H_{11}$ is an n-pentyl group.

Cannabichromene is naturally present (e.g. in *cannabis* plants) in its acid form (cannabichromenic acid) but may be decarboxylated to form the neutral cannabinoid, cannabichromene.

Formula 3 where $R^1$ is either H or COOH
C3H7 is an n-propyl group.

Cannabichromene propyl analogue, like cannabichromene, is naturally present as the acid but may be decarboxylated to the neutral form.

Preferably the compound(s) of formula 1 are present in the composition of the invention as an extract of at least one *cannabis* plant.

The term "*cannabis* plant(s)" encompasses wild type *Cannabis sativa* and also variants thereof, including *cannabis* chemovars (varieties characterised by virtue of chemical composition) which naturally contain different amounts of the individual cannabinoids, also *Cannabis sativa* subspecies indica including the variants var. indica and var.kafiristanica, *Cannabis* indica and also plants which are the result of genetic crosses, self-crosses or hybrids thereof. The term "*cannabis* plant material" is to be interpreted accordingly as encompassing plant material derived from one or more *cannabis* plants. For the avoidance of doubt it is hereby stated that "*cannabis* plant material" includes herbal *cannabis* and dried *cannabis* biomass.

Processes for the preparation of *cannabis* plant extracts suitable for incorporation into pharmaceutical dosage forms are described in WO 02/064109, the contents of which are incorporated herein by reference.

In one embodiment this extract may comprise substantially all the naturally occurring cannabinoids in said plant(s). In further embodiments the extract may be enriched for cannabichromene, i.e. contain a greater proportion of the total cannabinoid content as CBC, as compared to the cannabinoid composition of the plant material from which the "extract" was prepared. This enrichment may be achieved by selecting a fraction of an initial plant extract, which fraction is enriched.

The "*cannabis* plant extract" included in the composition of the invention will preferably contain at least 5%, preferably at least 10%, more preferably at least 20%, more preferably 30%, and even more preferably at least 40% of the total cannabinoid content as CBC.

Suitable examples of such CBC-enriched extracts are described in GB0222077.0. These are products derived from *cannabis* plant material, enriched in cannabichromene (CBC), with a chromatographic purity for CBC of greater than 85% by area normalisation of an HPLC profile. Methods for analysis of cannibinoid-containing extracts by HPLC and TLC are also described in GB0222077.0.

Enriched CBC extracts may be prepared from *cannabis* plant material using the process outlined below:

i) decarboxylating the *cannabis* plant material,
ii) preparing an extract of the decarboxylated *cannabis* plant material with hexane,
iii) filtering the resultant extract and removing solvent from filtrate by rotary evaporation to form an extract enriched in CBC,
iv) passing a solution of the resulting CBC enriched extract through a column packed with Sephadex-LH20™, eluting with 2:1 chloroform/dichloromethane,
v) collecting CBC rich fractions eluted from the column and removing solvent by rotary evaporation,
vi) re-dissolving the crude CBC obtained in step
v) in methanol, removing insoluble residue by filtration and removing solvent from filtrate by rotary evaporation,
vii) re-dissolving the product of step vi) in pentane, removing insoluble residue by filtration and removing solvent from filtrate by rotary evaporation to produce a highly enriched CBC extract.

*Cannabis* plant extracts for use in the compositions of the invention will may have other non-cannabinoid plant components, such as for example terpenes, removed.

In a still further embodiment the compound(s) of formula 1 may be isolated and substantially pure compounds, such as CBC or CBCV (as acids or in their neutral forms). Isolated and substantially pure cannabichromenes will be substantially free of other cannabinoids and other plant components such as, for example, terpenes. "Isolated and substantially pure cannabichromenes" may be of natural origin, i.e. isolated and purified from *cannabis* plant material, or may be synthetic compounds.

"Substantially pure" preparations of cannabinoid or cannabinoid acids are defined as preparations having a chromatographic purity (of the desired cannabinoid or cannabinoid acid) of greater than 95%, more preferably greater than 96%, more preferably greater than 97%, more preferably greater than 98%, more preferably greater than 99% and most preferably greater than 99.5%, as determined by area normalisation of an HPLC profile.

The compositions of the invention may be formulated for delivery nasally, sublingually, buccally, topically, orally, rectally, intravenously, intra-peritoneally, intra-muscularly, subcutaneously, transdermally, intra-vaginally, intra-urethrally, by nebuliser, as inhaled vapour or by installation directly into the bladder. They may be in liquid or solid dosage form and may include, in addition to the active, other pharmaceutically acceptable components such as an excipients, solvents, diluents, fillers, salts, buffers, stabilizers, solubilizers, etc. The dosage form may contain other pharmaceutically acceptable excipients for modifying conditions such as pH, osmolarity, taste, viscosity, sterility, lipophilicity, solubility etc. The choice of diluents, carriers or excipients will depend on the desired dosage form, which may in turn be dependent on the intended route of administration to a patient.

Solid dosage forms include, for example, tablets, capsules, powders, dispersible granules, cachets and suppositories, including sustained release and delayed release formulations. Powders and tablets will generally comprise from about 5% to about 70% active ingredient. Suitable solid carriers and excipients are generally known in the art and include, e.g. magnesium carbonate, magnesium stearate, talc, sugar, lactose, etc. Tablets, powders, cachets and capsules are all suitable dosage forms for oral administration.

Liquid dosage forms include solutions, suspensions and emulsions. Liquid form preparations may be administered by intravenous, intracerebral, intraperitoneal, parenteral or intramuscular injection or infusion. Sterile injectable formulations may comprise a sterile solution or suspension of the active agent in a non-toxic, pharmaceutically acceptable diluent or solvent. Liquid dosage forms also include solutions or sprays for intranasal, buccal or sublingual administration.

Aerosol preparations suitable for inhalation may include solutions and solids in powder form, which may be combined with a pharmaceutically acceptable carrier, such as an inert compressed gas.

Also encompassed are dosage forms for transdermal administration, including creams, lotions, aerosols and/or emulsions. These dosage forms may be included in transdermal patches of the matrix or reservoir type, which are generally known in the art.

Pharmaceutical preparations may be conveniently prepared in unit dosage form, according to standard procedures of pharmaceutical formulation. The quantity of active compound per unit dose may be varied according to the nature of the active compound and the intended dosage regime. Generally this will be within the range of from 0.1 mg to 1000 mg.

Preferably the pharmaceutical compositions of the invention may be used in the treatment of mood disorder conditions such as morbid or clinical depression, unipolar mood disorder, bipolar mood disorder, syndromal depression, panic disorder or anxiety.

The invention further relates to a method of treating a mood disorder, such as morbid or clinical depression, unipolar mood disorder, bipolar mood disorder, syndromal depression, panic disorder or anxiety, in a human patient, which comprises administering to a patient in need thereof a therapeutically effective amount of a compound of Formula 1 as defined herein, preferably in the form of a pharmaceutical composition according to the invention.

The terms "treating" or "treatment" as used herein with reference to therapeutic uses of compounds of general formula 1 describe the management or care of a patient for the purposes of combatting disease, and includes the administration of the active agent to asymptomatic individuals, for example to prevent the onset of the symptoms or complications, i.e. prophylaxis.

The active agents are to be administered to human subjects in "therapeutically effective amounts", which is taken to mean a dosage sufficient to provide a medically desirable result in the patient. The exact dosage and frequency of administration of a "therapeutically effective amount" of active agent will vary, depending on the condition which it is desired to treat, the stage and severity of disease, and such factors as the nature of the active substance, the dosage form and route of administration. A typical dosage range for compounds of general formula 1 is in the range of from 10-80 mg of compound per kg of mammal by weight, with 20 mg/kg having been shown to be a particularly effective dosage in mice. However, it is not intended to limit the invention to doses in this range. The appropriate dosage regime for a given patient will generally be determined by a medical practitioner having regard to such factors as the severity of disease, and the age, weight and general physical condition of the patient, and the intended duration of treatment, as would be appreciated by those skilled in the art.

Cannabichromene (CBC) is one of more than 60 cannabinoids known to occur in *cannabis* (Turner et al., 1980). CBC is the forth major cannabinoid in *cannabis* and is predominantly found to occur in tropical strains of *Cannabis* sp. In hemp varieties, CBC and cannabidiol (CBD) are the most predominant cannabinoids that accumulate.

The biosynthetic pathway of CBC begins with the condensation of geranyl phosphate with a precursor of olivetolic acid, which is possibly a $C_{12}$ polyketide derived from acetate or malonate (Turner and Mahlberg, 1985). This produces an intermediate from which cannabichromenic acid (CBCA) forms.

Figure 1:
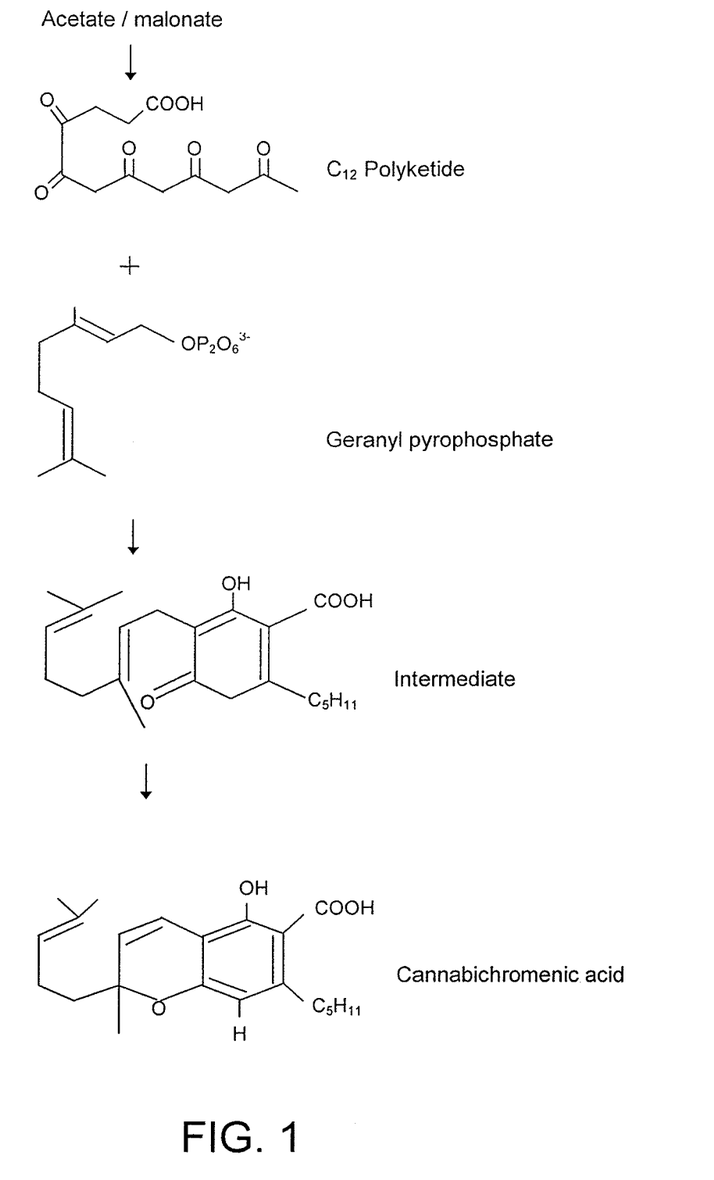
FIG. 1 shows the biosynthetic pathway for CBCA.

FIG. 1 shows the biosynthetic pathway for CBCA.

The formation of Cannabidiolic acid (CBDA) occurs via a different route of the pathway, whereby the geranyl pyrophosphate condenses with olivetolic acid to produce cannabigerolic acid (CBGA). It is thought that CBGA then forms a transition state molecule, which can then form either CBCA or CBDA. CBDA is the precursor to the tetrahydrocannabinolic acids (THCA) but is itself only mildly psychoactive. CBC is also only mildly psychoactive and may interact synergistically with THC to alter the psychoactive effects (Turner et al., 1975). It is thought that CBD may suppress the effect of THC and that CBC may potentiate the effect of THC. Total psychoactivity of *cannabis* is attributed to the ratios of the primary cannabinoids THC, CBD, CBN and CBC.

There are several known actions of CBC as discussed below in comparison to those actions known for other cannabinoids;

Similarly to CBD, CBC decreases inflammation (Wirth et al., 1980). CBC was tested in vivo using the rat paw edema test and in vitro using the erythrocyte membrane stabilization assay. It was shown that CBC was as effective as phenylbutazone (PBZ) at equivalent doses. The authors surmised that as CBC is less toxic than PBZ and larger doses might be given to produce a greater therapeutic effect.

CBC has been shown to inhibit prostaglandin synthesis in vitro but less potently than THC or CBD (Burstein et al., 1973). The order of activity starting with the most potent was cannabinol, cannabidiolic acid, delta-6-tetrahydrocannabinol (Δ6-THC), cannabidiol, cannabichromene and Δ1-THC. Cannabicyclol showed almost no inhibitory activity. The authors suggest that some of the pharmacological actions of these prostaglandin inhibiting cannabinoids may be explained by a similar effect in vivo. Olivetol, which represents a partial structure for all of the compounds tested, showed high activity, suggesting that the inhibitory power of the cannabinoids resides in the aromatic portion of the molecule.

A review of the natural constituents of *cannabis* reported that CBC causes sedation in dogs and decreased muscular coordination in rats but has not been shown to cause any cannabimimetic activity in monkeys or humans (Turner et al., 1980).

The co-administration of CBC with THC to rats potentiates the THC changes in heart rate but does not potentiate THC's hypotensive effects, in mice the co-administration of THC and CBC lowers the $LD_{50}$ of THC (Hatoum et al., 1981). The $LD_{50}$ in mice after single intraperitoneal (i.p.) doses of cannabichromene (CBC) and Δ9-THC were 113.4 and 276.3 mg/kg, respectively. A small dose (25 mg/kg) of CBC given concurrently with Δ9-THC lowers the $LD_{50}$ of Δ9-THC to 152.0 mg/kg.

Unlike the psychoactive derivatives of *cannabis* such as THC, CBC is not scheduled under the Misuse of Drugs Act 1971.

There have been many reports about the negative psychological side effects of *cannabis* and as a result there has been little attention paid to the therapeutic potential in the treatment of psychological disorders.

Some patients have found *cannabis* to be useful in the treatment of anxiety, depression and bipolar disorder (Zimmerman, 1998). However reports on the therapeutic potential of *cannabis* are often contradictory as they describe the effects of whole, usually smoked, *cannabis* rather than the actions of the specific cannabinoids themselves.

In a case study published in 1996 observations provided some evidence that whole, smoked *cannabis* was responsible for antidepressant effects in individuals with mood disorder (Gruber et al., 1996). The paper presents five case studies in which *cannabis* exerted an antidepressant effect, all five patients reported that *cannabis* relieved their symptoms and that they used it for that purpose.

The present invention is further described, by way of example only, with reference to the following example and FIGS. 2-10.

EXAMPLE

A substantially pure extract of cannabichromene (Formula 2) was studied for it's ability to modify the behaviour of mice during a tail suspension test in comparison with those changes brought about by imipramine a known antidepressant.

Materials and Methods:

The experiment used 112 C57BL6BYJ mice (Jackson Laboratories, Bar Harbor, Me.) which were housed in same sex groups (n=3-5) and maintained on a reversed 12 h light-dark cycle, with all testing being completed during the first 4 h of the dark phase cycle. Food and water were provided ad libitum except during behavioural testing. The subjects were six weeks old at the time of testing and consisted of groups with equal numbers of males (18-26 g) and females (15-21 g).

Figure 8:
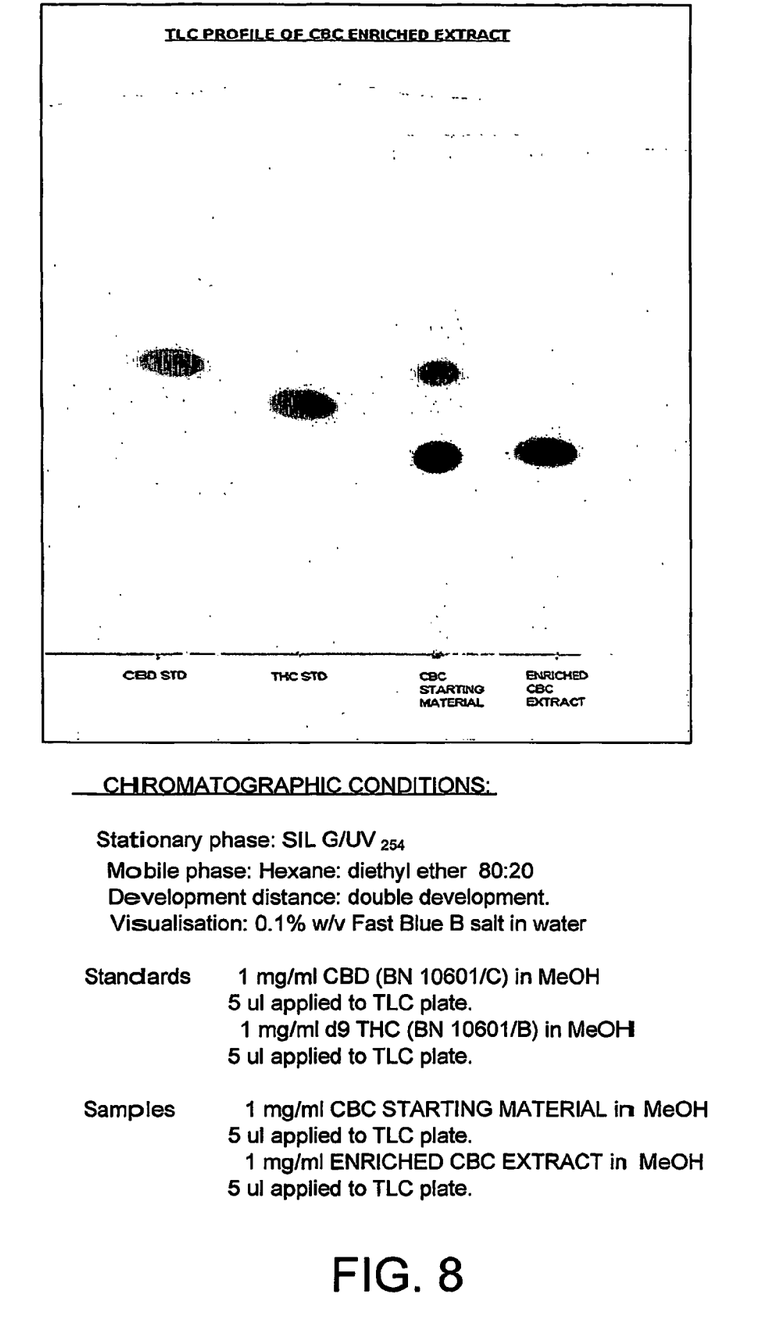
FIG. 8 shows TLC profiles of an enriched CBC extract and starting material (extract of a G80 *cannabis* chemovar-decarboxylated) compared to CBD and $Δ^9$ THC standards.

The substantially pure CBC (FIG. 8 shows chromatograms illustrating the purity of this material) was isolated from a botanical extract of a high CBC containing *cannabis* chemovar which was obtained using conventional selective breeding techniques. Using such traditional selective breeding techniques the applicant has been able to select *cannabis* varieties (chemovars) having a relatively high content of CBC. General protocols for growing medicinal *cannabis* and for testing the cannabinoid content of *cannabis* plants are described in the applicant's published International patent application WO 02/064109. The botanical raw material (BRM) was subjected to supercritical $CO_2$ extraction and winterisation to remove waxes, as described in the applicant's patent application GB02181901.7.

The resulting extract was further purified by a series of chromatographic steps as described below and in the applicant's patent application number GB0222077.0. This involved:

i) dissolving the extract in hexane;
ii) filtering the resultant extract and removing solvent from filtrate by rotary evaporation to form an extract enriched in CBC;
iii) passing a solution of the resulting CBC enriched extract through a column packed with Sephadex-LH20™, eluting with 2:1 chloroform/dichloromethane;
iv) collecting CBC rich fractions eluted from the column and removing solvent by rotary evaporation;
v) re-dissolving the crude CBC obtained in step v) in methanol, removing insoluble residue by filtration and removing solvent from filtrate by rotary evaporation;
vi) re-dissolving the product of step vi) in pentane, removing insoluble residue by filtration and removing solvent from filtrate by rotary evaporation to produce a highly enriched CBC extract;
vii) subjecting the highly enriched CBC extract to flash chromatography to produce a substantially pure CBC extract of >98% w/w.

Figure 9:
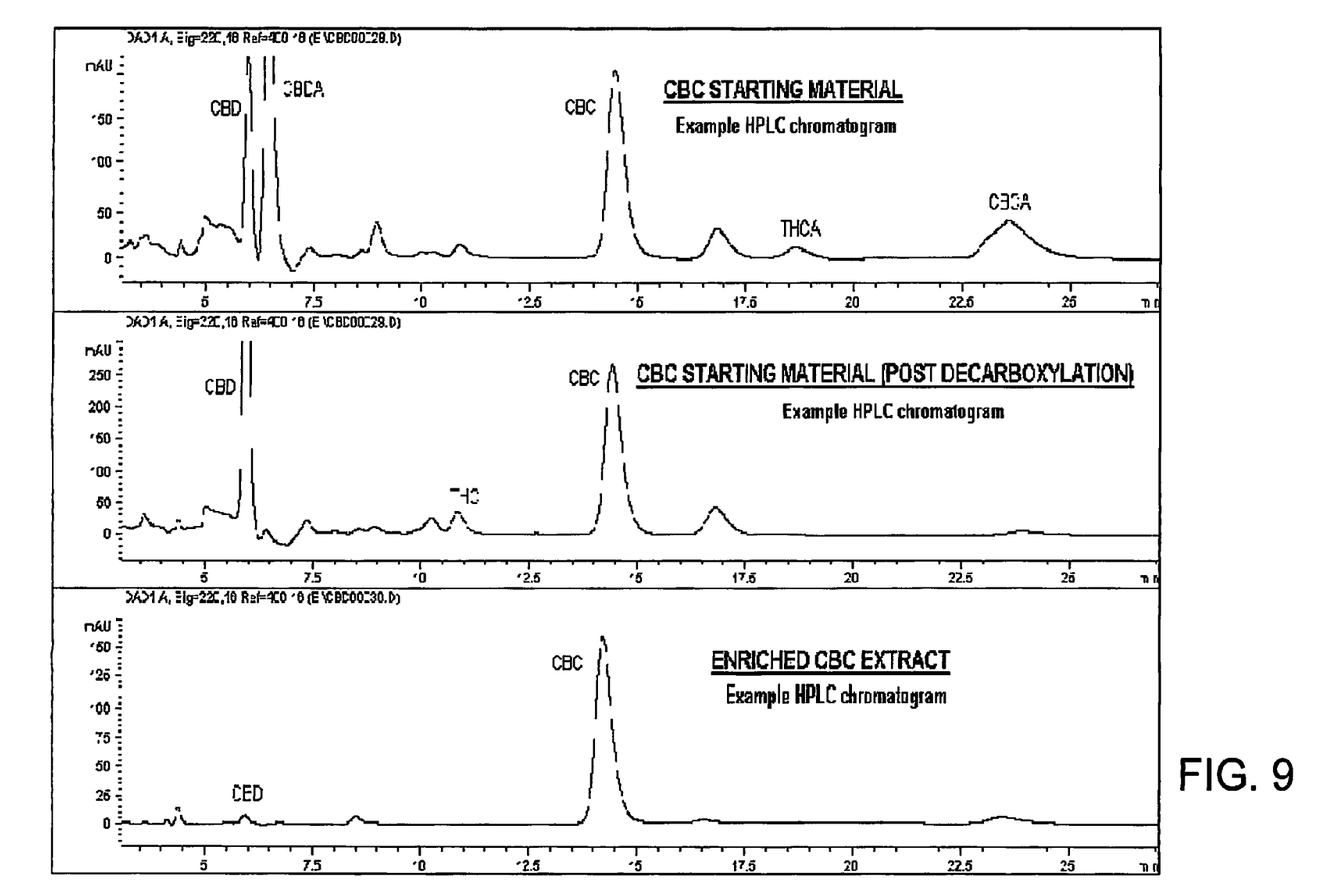
FIG. 9 shows HPLC profiles of enriched CBC extract and starting material (extract of a G80 *cannabis* chemovar-decarboxylated).
Figure 10:
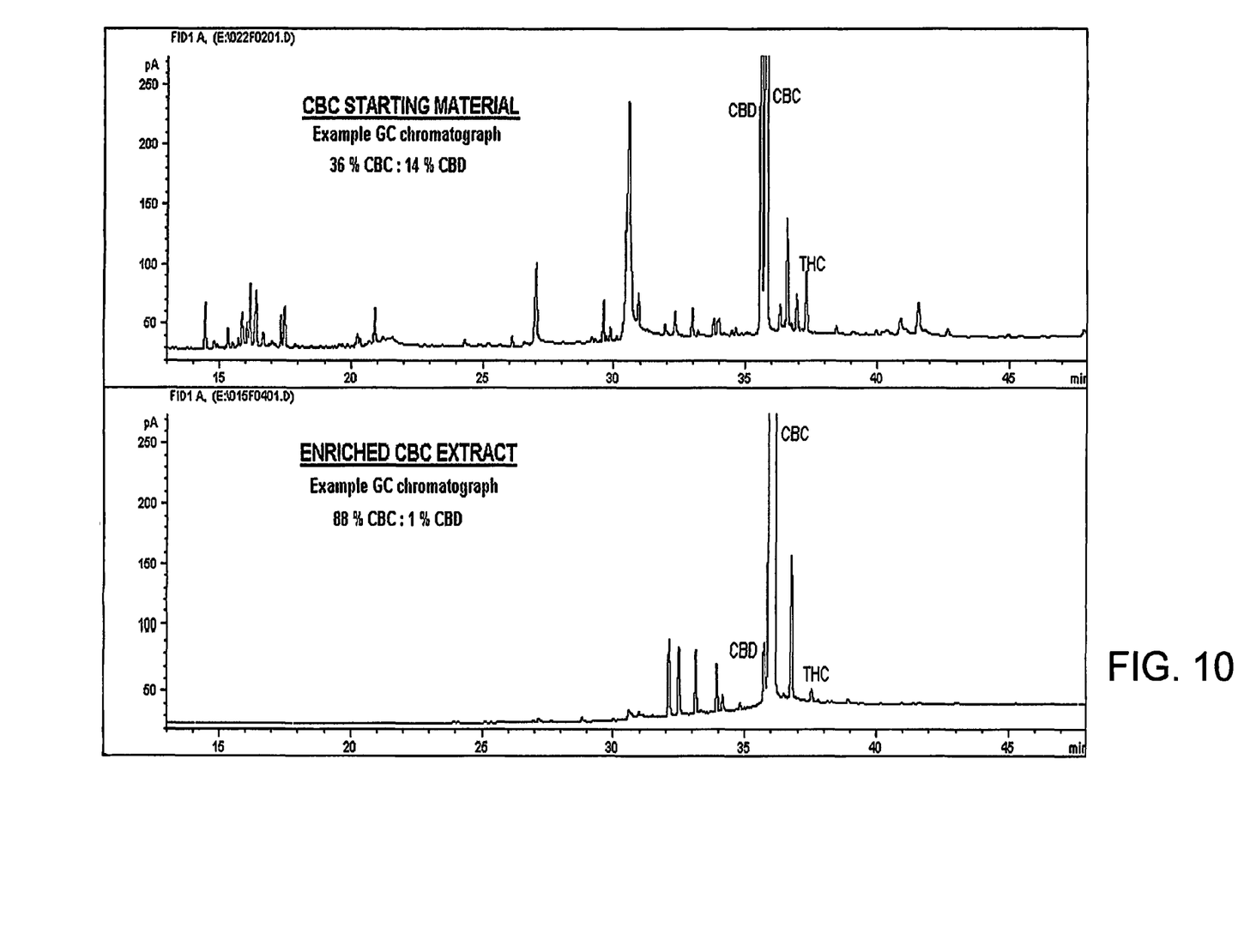
FIG. 10 shows GC profiles of enriched CBC extract and starting material (extract of a G80 *cannabis* chemovar-decarboxylated).

TLC, HPLC and GC chromatograms are shown as FIGS. 8-10.

The substantially pure CBC extract (54.0 mg/ml in ethanol) was diluted in Tween 80 and subsequently diluted further to the correct dose with PBS (pH 7.4). The final concentration of Tween 80 was 5% for all preparations.

Imipramine (30 mg/kg) was used as an antidepressant control and diluted as per the CBC extract. Test article at doses of 0, 5, 10, 20, 40, 80 mg/kg/0.01 ml/g bodyweight were administered i.p. under sodium light to minimise exposure to light.

For the tail suspension test, a sound-attenuated chamber (Lafayette Instruments, Lafayette, Ind.) with a titanium bar (1 cm diameter×24 cn long) mounted 15 cm from the floor of the test chamber was used. An opto-electronic sensor was mounted in a 4 cm×4 cm white plastic column and positioned 5 cm from the mounting bar. An infra-red light transmitted from the light emitting diode onto the animal. If the animal moved, the amount of light collected by the phototransistor would increase or decrease depending on the size and duration of the movement. The opto-electric sensor was connected to an interface designed to condition and amplify the signal (range 0-10 volts) and then send the amplified signal to an A/D interface board (Powerlab 4/s: AD Instruments, Mountain View, Calif.) connected to a Macintosh G4 microcomputer. The duration of the experiment and the recording of raw behavioural responses was controlled and saved to a data file using Chart 3.6 data collection software (AD Instruments, Mountain View, Calif.).

The open-field apparatus consisted of a 44.5×44.5×30 cm chamber with clear plastic walls and a white plastic floor (Med Associates mode #ENV515, St. Albans, Vt.). Behaviours were recorded using a Quasar video recorder suspended above the chamber. The chamber was divided into four equal sized quadrants during scoring by placing a clear plastic template on the video screen during scoring. Behaviours were scored using data collection software. The room cues remained constant throughout testing, room temperature was 22° C.

On the day of testing, the mice were weighed and randomly assigned to groups with the restriction that equal numbers of males and females be represented in each group. Test article or control drug was injected intraperitoneally. Thirty minutes later each mouse was tested on the tail-suspension test for six minutes.

The mouse was suspended from a bar by the tail using adhesive tape so that the tip of their nose was 2 cm from the floor of the tail suspension chamber. The photodiode was then placed 5 cm away from the subject and aimed at the middle of the subject's ventral surface. Each subject was tested for six minutes. The total number of movements and total amount of time spent immobile were recorded. A movement was scored if the amount of light deflected resulted in a change of 350 mV or more from baseline for at least 5 ms. We have found that changes of less than 350 mV usually indicated artefacts (e.g. breathing) and not voluntary movements. A period of immobility was counted only if no movements above 350 mV were recorded for at least 1000 ms. The total amount of time spent immobile was calculated by summing the duration of the individual immobility periods. These criteria were selected to be similar to those used in previous tail suspension studies (e.g., Steru et al., 1985).

Immediately after the tail suspension test (36-38 minutes after treatment with test article or control), each mouse was individually placed in the open-field chamber for a five minute videotaped test session. Videotapes were later scored by observers who were unaware of the subject's group assignment. The frequency of crossings, rears, grooming and defecation were recorded for each subject. A crossing response was scored when an animal moved all four paws into any quadrant in the test chamber. A rearing response was scored when an animal stood erect on the two rear legs with both front paws lifted off the floor. Grooming was scored according to the criteria used in previous rodent studies (Walsh & Cummins, 1976).

Mice stereotypically begin by licking the forepaws, then use the forepaws to clean the face and ears and then the trunk and hindquarters. A single grooming response was scored at the beginning of this stereotyped pattern. The animal was required to engage in another behaviour (e.g., rearing) between bouts of grooming for the subsequent behaviour to be scored as a separate response. This method controlled for any possible distractions that might cause the animal to pause prior to completing the grooming pattern and thereby minimizes the possibility of artificially increasing the frequency of grooming responses.

Results:

Antidepressant effects are indicated by an increase in the frequency of struggling activity during the test. In addition the degree or amplitude of struggling is thought to be a predictor of antidepressant activity.

The results shown in FIGS. 2 to 7 are from the male mice only as the data obtained from the female mice were confounded by the oestrous cycle.

Figure 2:
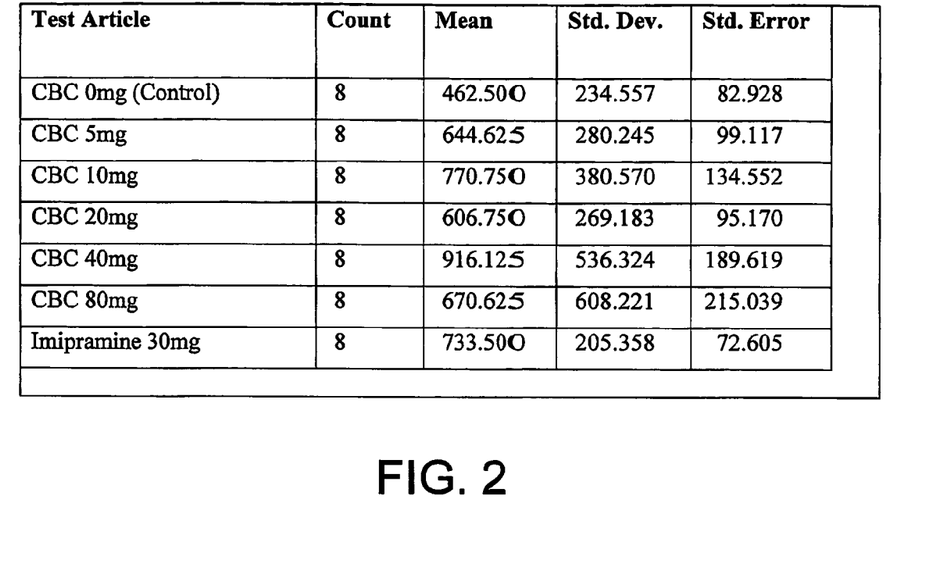
FIG. 2 is a means table for all activity recorded in the tail suspension test for CBC at 0, 5, 10, 20, 40, 80 mg/kg/0.01 ml/g bodyweight and imipramine at 30 mg/kg/0.01 ml/g bodyweight.
Figure 3:
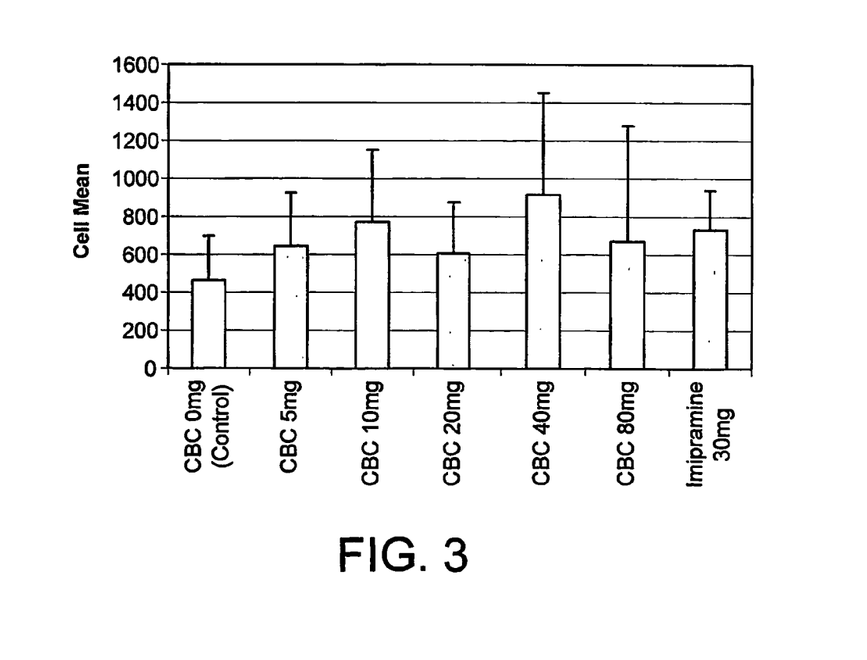
FIG. 3 is an interaction bar plot for all activity for CBC at 0, 5, 10, 20, 40, 80 mg/kg/0.01 ml/g bodyweight and imipramine at 30 mg/kg/0.01 ml/g bodyweight.

FIGS. 2 and 3 detail all activity recorded in the tail suspension test for CBC at 0, 5, 10, 20, 40, 80 mg/kg/0.01 ml/g bodyweight and imipramine at 30 mg/kg/0.01 ml/g bodyweight. This table shows that in comparison to the control where neither CBC nor imipramine were given all doses increased the mean activity level of the mice in the test. The largest activities were seen in those mice dosed with 40 mg CBC/kg/0.01 ml/g bodyweight. Activity levels comparable to those observed in the mice administered imipramine were observed in those mice dosed at 10 mg CBC/kg/0.01 ml/g bodyweight. From these figures it can be inferred that CBC at a dose of 40 mg/kg/0.01 ml/g bodyweight is a more potent antidepressant than imipramine.

Figure 4:
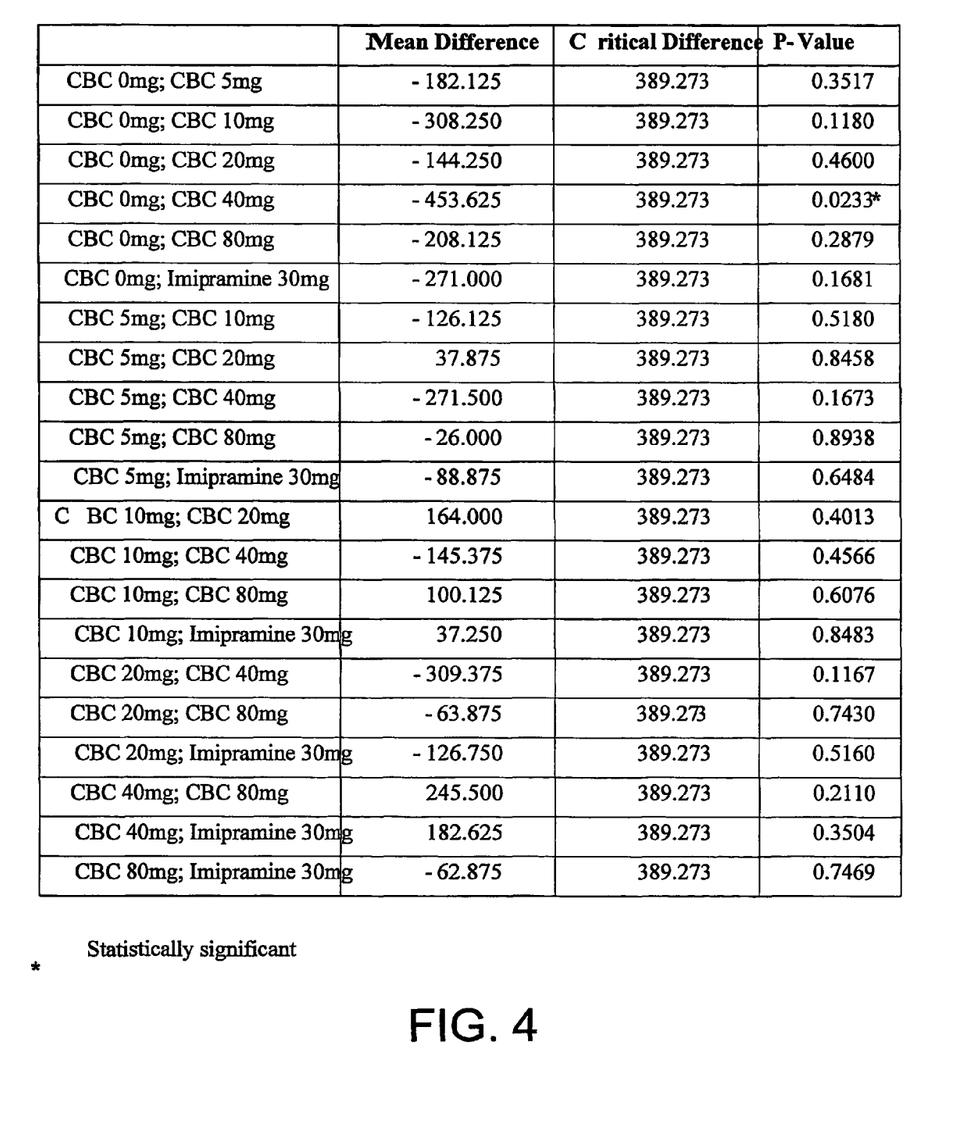
FIG. 4 is a Fishers PLSD table for all activity for CBC at 0, 5, 10, 20, 40, 80 mg/kg/0.01 ml/g bodyweight and imipramine at 30 mg/kg/0.01 ml/g bodyweight.

FIG. 4 is a table detailing the Fisher's PLSD for all activity observed during the mouse tail suspension test. The significant value observed from the statistical analysis is that of the CBC at 40 mg/kg/0.01 ml/g bodyweight versus the control at 0 mg CBC/kg/0.01 ml/g bodyweight. As was suggested by the previous data, CBC at a dose of 40 mg/kg/0.01 ml/g bodyweight is a more potent antidepressant than imipramine.

Figure 5:
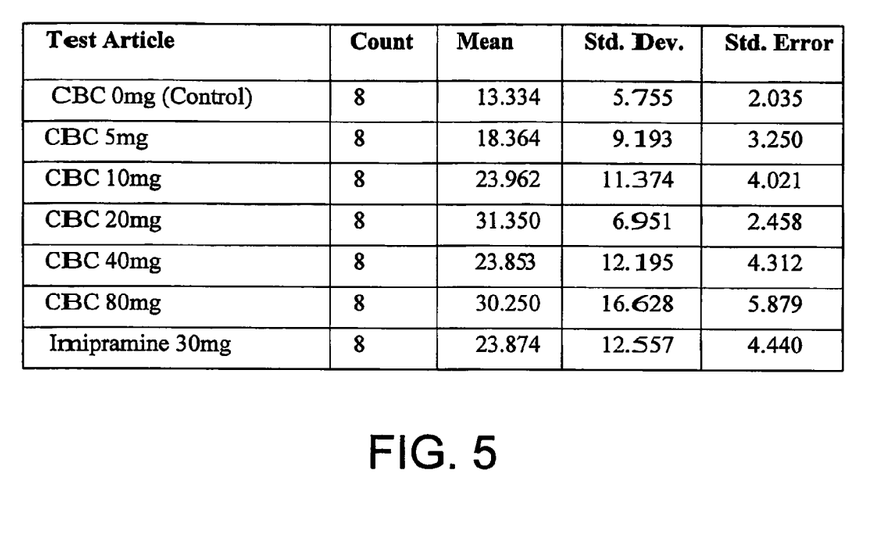
FIG. 5 is a means table for the percentage of animals showing very large vigorous movements for CBC at 0, 5, 10, 20, 40, 80 mg/kg/0.01 ml/g bodyweight and imipramine at 30 mg/kg/0.01 ml/g bodyweight.
Figure 6:
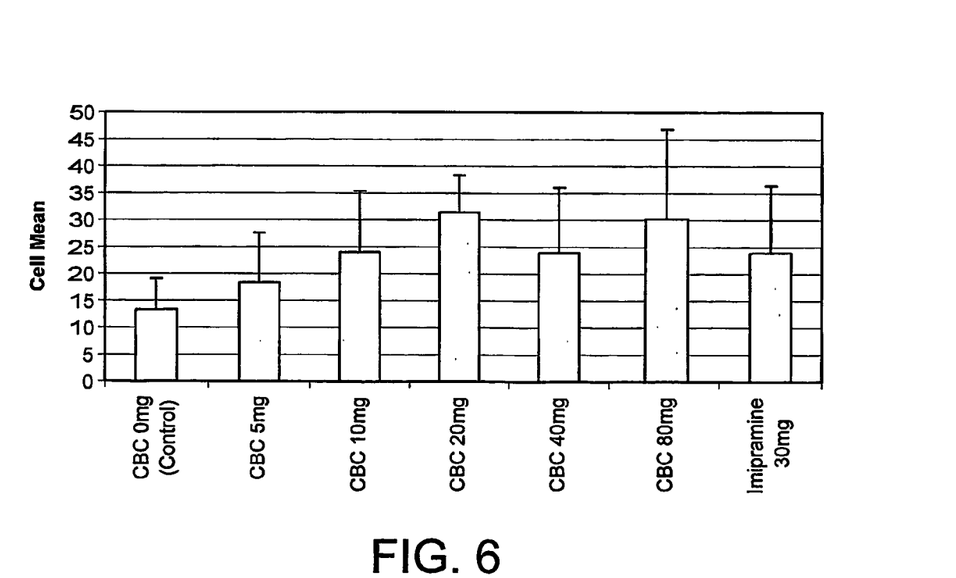
FIG. 6 is an interaction bar plot for the percentage of animals showing very large vigorous movements for CBC at 0, 5, 10, 20, 40, 80 mg/kg/0.01 ml/g bodyweight and imipramine at 30 mg/kg/0.01 ml/g bodyweight.

FIGS. 5 and 6 detail the percentage of animals showing very large vigorous movements or "struggling" for CBC at 0, 5, 10, 20, 40, 80 mg/kg/0.01 ml/g bodyweight and imipramine at 30 mg/kg/0.01 ml/g bodyweight. These data show that CBC administered at a dose of either 20 or 80 mg/kg/0.01 ml/g bodyweight produced a greater number of large vigorous movements in the animals than imipramine at a dose of 30 mg/kg/0.01 ml/g bodyweight. Doses of 10 and 40 mg/kg/0.01 ml/g bodyweight produced a comparable number of large vigorous movements in the mice as were recorded for imipramine. These data suggest that the administration of CBC results in an increased percentage of struggling behaviour, which is an indicator of antidepressant activity.

Figure 7:
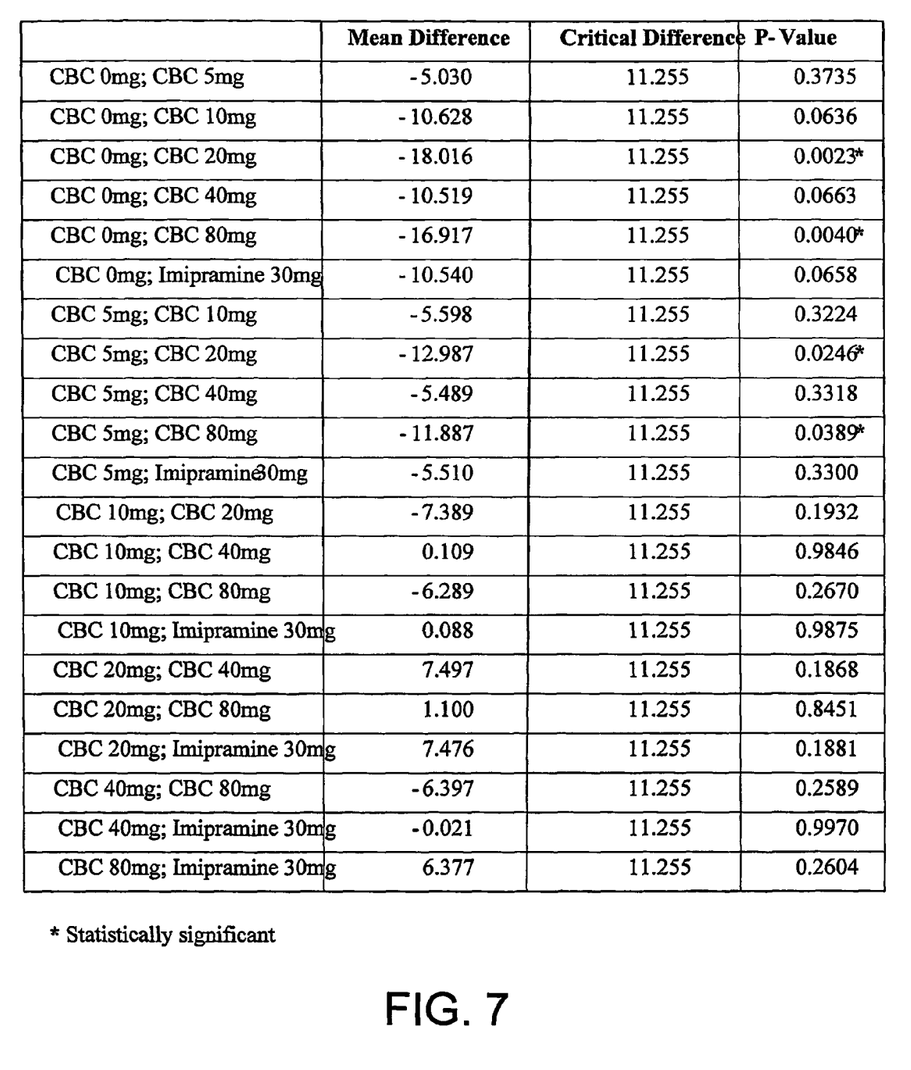
FIG. 7 is a Fishers PLSD table for the percentage of animals showing very large vigorous movements for CBC at 0, 5, 10, 20, 40, 80 mg/kg/0.01 ml/g bodyweight and imipramine at 30 mg/kg/0.01 ml/g bodyweight.

FIG. 7 is a table detailing the Fisher's PLSD for the percentage of animals showing very large vigorous movements or "struggling" as were observed during the mouse tail suspension test. The statistical analysis identified sever-al significant data. Most significant was that of the CBC at 20 mg/kg/0.01 ml/g bodyweight versus the control at 0 mg CBC/kg/0.01 ml/g bodyweight. Other statistically significant data was that of is that of the CBC at 20 mg/kg/0.01 ml/g bodyweight versus CBC at 5 mg/kg/0.01 ml/g bodyweight and CBC at 80 mg/kg/0.01 ml/g bodyweight versus CBC at 5 mg/kg/0.01 ml/g bodyweight. The data analysed here indicates that a dose of CBC between 10 and 80 mg/kg/0.01 ml/g bodyweight produces antidepressant action in the mouse tail suspension test and that the most efficient dose is 20 mg/kg/0.01 ml/g bodyweight.

Interpretation:

The data presented suggest that CBC may induce antidepressant effects. From the data shown in the figures it can be seen that moderate doses of CBC produced behaviours that were consistent with imipramine in the tail suspension test. A dose of 40 mg CBC/kg/0.01 ml/g bodyweight resulted in an elevated activity mean of 916.1 compared to the activity mean for imipramine (30 mg/kg/0.01 ml/g bodyweight) being 733.5 and the control mean being 462.5. Additionally it was noted that those mice that were administered with CBC showed an increase in the amplitude of struggling behaviour. Significant increases in the degree of struggling were found between the vehicle control (mean=13.3%), the 20 mg/kg/0.01 ml/g bodyweight CBC dose (mean=31.4%) and the 80 mg/kg/0.01 ml/g bodyweight CBC dose (mean=30.2%).

References:

Burstein S, Varanelli C and Slade L T (1973) Prostaglandins and *Cannabis*-II. Inhibition of biosynthesis by the naturally occurring cannabinoids. Biochem Pharmacol. 22, 2905-2910

Gruber A J, Pope H G, Brown M E (1996) Do patients use marijuana as an antidepressant? Depression, 4, 77-80

Hatoum N S, Davis W M, ElSohly M A, Turner C E (1981) Cannabichromene and delta-9-tetrahydrocannabinol:interactions relative to lethality, hypothermia and hexobarbital hypnosis. Gen. Pharmacol. 12, 357-362

Steru L, Chermat R, Thierry B, Simon P (1985) The tail suspension test: a newmethod for screening antidepressants in mice. Psychpharmacology (Berl). 85(3), 367-360

Turner J C and Mahlberg P G (1985) Cannabinoid synthesis in *Cannabis sativa* L. Am. J. Bot., 72(6), 911

Turner C E, Fetterman P S, Hadley K W, Urbanek J E (1975) Constituents of *Cannabis sativa* L. X: Cannabinoid profile of a Mexican variant and its possible correlation to pharmacological activity. Acta Pharm. Jugoslav., 25, 7-16

Turner C E, ElSohly M A and Boeren E G (1980) Constituents of *Cannabis sativa* L. XVII. A review of the natural constituents. J. Nat. Prod., 43(2), 169-234

Walsh R N and Cummins R A (1976) Mechanisms mediating the production of environmentally induces brain changes. Psychol. Bull. 82(6), 986-1000

Wirth P W, Watson E S, ElSohly M A, Turner C E, Murphy J C (1980) Anti-inflammatory properties of cannabichromene. Life Sci. 26, 1991-1995

Zimmerman B, Bayer R, Crumpacker N (1998) Is Marijuana the right medicine for you? A factual guide to the medical uses of marijuana. Keats Publishing. USA 166-167

The invention claimed is:

1. A method for treating depression in a human patient, which comprises administering to a patient in need thereof a therapeutically effective amount of cannabichromene (CBC) wherein the CBC is substantially pure or is an extract from a cannabis plant that contains greater than or equal to 30% CBC of the total cannabinoid content, and wherein the CBC is administered as a unit dosage form that comprises CBC in an amount of 0.1 mg to 1000 mg.

2. The method according to claim 1 wherein the CBC is present in an extract of at least one cannabis plant.

3. The method according to claim 1, wherein the CBC is administered nasally, sublingually, buccally, topically, orally, rectally, intravenously, intra-peritoneally, intra-muscularly, subcutaneously, transdermally, intra-vaginally, intra-urethrally, by nebuliser, as inhaled vapour or by installation directly into the bladder.

4. The method according to claim 2, wherein the extract comprises substantially all the naturally occurring cannabinoids in said at least one cannabis plant.

5. The method according to claim 2, wherein the extract is enriched for CBC.

6. The method according to claim 1, wherein the CBC is administered in an isolated and substantially pure form.

7. The method according to claim 1, wherein the CBC is administered together with one or more pharmaceutically acceptable diluents, excipients or carriers.

8. The method according to claim 1, wherein the CBC is not administered as inhaled vapour.

* * * * *